(12) United States Patent
Porter

(10) Patent No.: US 7,485,123 B2
(45) Date of Patent: Feb. 3, 2009

(54) COMPLEX VASO-OCCLUSIVE COILS

(75) Inventor: Stephen C. Porter, Oakland, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 533 days.

(21) Appl. No.: 10/790,982

(22) Filed: Mar. 1, 2004

(65) Prior Publication Data

US 2005/0192618 A1    Sep. 1, 2005

(51) Int. Cl.
*A61B 17/24* (2006.01)

(52) U.S. Cl. ...................................... 606/113

(58) Field of Classification Search ................ 606/113, 606/114, 127, 159, 151, 157, 191–200
See application file for complete search history.

(56) References Cited

U.S. PATENT DOCUMENTS

| | | | |
|---|---|---|---|
| 4,994,069 A | 2/1991 | Ritchart et al. | |
| 5,911,731 A | 6/1999 | Pham et al. | |
| 6,322,576 B1 * | 11/2001 | Wallace et al. | 606/191 |
| 6,605,101 B1 | 8/2003 | Schaefer et al. | |
| 6,635,069 B1 * | 10/2003 | Teoh et al. | 606/200 |
| 6,929,654 B2 * | 8/2005 | Teoh et al. | 606/200 |
| 7,029,486 B2 * | 4/2006 | Schaefer et al. | 606/191 |
| 2002/0019847 A1 | 2/2002 | Wallace et al. | |

FOREIGN PATENT DOCUMENTS

| | | |
|---|---|---|
| EP | 0 739 605 A | 10/1996 |
| EP | 1 219 246 A | 7/2002 |
| WO | WO 01/93937 A | 12/2001 |
| WO | WO 03/059176 A | 7/2003 |

OTHER PUBLICATIONS

PCT International Search Report for PCT/US2005/003592, Applicant: Boston Scientific Scimed, Inc., Forms PCT/ISA/210 and 220, dated Jun. 9, 2005 (9 pages).
PCT Written Opinion of the International Search Authority for PCT/US2005/003592, Applicant: Boston Scientific Scimed, Inc., Form PCT/ISA/237, dated Jun. 9, 2005 (6 pages).

* cited by examiner

*Primary Examiner*—Kevin T Truong
(74) *Attorney, Agent, or Firm*—Vista IP Law Group, LLP

(57) ABSTRACT

A vaso-occlusive device includes a member that forms a series of at least four successive loops, each loop of the series having a different axis than, and lying in a separate plane from, any other loop of the series. Each plane in which a loop lies forms an angle greater than 30 degrees with any immediately proceeding, and any immediately succeeding, plane.

10 Claims, 3 Drawing Sheets

COMPLEX VASO-OCCLUSIVE COILS

FIELD OF THE INVENTION

The present invention relates generally to vaso-occlusive devices, and more particularly, to vaso-occlusive coils having out-of-plane helical elements.

BACKGROUND OF THE INVENTION

Vaso-occlusive devices are surgical implants that are placed within an opening in the vasculature which is to be occluded, such as, for example, within an aneurismal cavity to form an embolus by blocking the flow of blood. Vaso-occlusive devices are typically delivered and placed at a selected site in the vasculature using a catheter in a minimally invasive procedure. In order to create an embolus, numerous coils are implanted in the site, e.g., an aneurysm, until an adequate density has been achieved.

Vaso-occlusive coils are usually constructed of a wire made of a metal or metal alloy wound into a helix. Such vaso-occlusive coils are typically manufactured to assume a certain shape upon discharge of the device from a distal end of a catheter into a treatment site. The shape of these coil is defined by the shape of the coil in a "free energy state," that is a state where there are no outside forces acting on the coil. A variety of such vaso-occlusive coils are known. For instance, U.S. Pat. No. 4,994,069, issued to Ritchart et al., describes a vaso-occlusive coil that assumes a linear helical configuration when stretched and a folded, convoluted configuration when released from the catheter. The stretched condition is used in placing the coil at the desired site via passage through the catheter. The coil assumes a relaxed configuration—which is better suited to occlude the vessel—once the device is released from the catheter. Ritchart et al., describes a variety of secondary shapes including "flower" shapes and double vortices. Unlike vaso-occlusive coils used prior to that time, Ritchart et al. discloses using a coil that is relatively soft and is delivered to the site using a pusher within a catheter lumen. Upon discharge from the delivery catheter, the coil may undertake a number of random or pre-determined configurations useful to fill the site.

Known vaso-occlusive coils may be used for filling relatively small vessel sites, e.g., 0.5-6.0 mm in diameter. The coils themselves are described as being between 0.254 and 0.762 mm in diameter. The length of the wire making up the vaso-occlusive coil is typically 15 to 40 times the diameter of the vessel to be occluded. The wire used to make up the coils may be, for instance, 0.051 to 0.152 mm in diameter. Tungsten, platinum, and gold threads or wires are typically preferred. Such coils may be easily imaged radiographically, readily located at a well defined vessel site, and retrieved, if necessary.

In order for vaso-occlusive coils to be most effective, it is desirable for the coils to fill a peripheral shell of the aneurysm. Ideally, the coils fill the void in a complex, but semi-uniform manner. However, because numerous coils are implanted, it is desirable that the coils do not become overly intertwined or otherwise prevent additional coils from being inserted.

SUMMARY OF THE INVENTION

In one embodiment of the invention, a vaso-occlusive device comprises a member that forms a series of at least four successive loops, each loop of the series having a different axis than, and lying in a separate plane from, any other loop of the series. Each plane forms an angle greater than 30 degrees with any immediately proceeding and any immediately succeeding plane. By way of non-limiting example, each plane may form an angle between 45 and 90 degrees with any immediately proceeding and any immediately succeeding plane. By way of another, non-limiting example, each plane may be perpendicular to any immediately proceeding and any immediately succeeding plane.

The loops may be helical, elliptical, oval, or some other shape or combination of shapes. A pair of successive loops of the series may be connected by a linear member. In one embodiment, a distal most loop of the series having a diameter smaller than a diameter of an immediately preceding loop.

Other aspects and features of the invention will be evident from reading the following detailed description of the illustrated embodiments, which are intended to illustrate, not limit, the invention.

BRIEF DESCRIPTION OF THE DRAWINGS

The drawings illustrate the design and utility of embodiments of the invention, in which similar elements are referred to by common reference numerals, and in which.

DETAILED DESCRIPTION OF THE ILLUSTRATED EMBODIMENTS

Various embodiments of the invention are described hereinafter with reference to the figures. It should be noted that the figures are not drawn to scale, and are intended only to facilitate the description of specific embodiments of the invention, not as an exhaustive description. Various aspects, features, and advantages described in conjunction with a particular illustrated embodiment are not necessarily limited to that embodiment, but may be practiced with other embodiments, even if not so illustrated or specifically described herein.

The complex coil designs of the invention are particularly useful in treating aneurysms. The shape provided herein results in an improved blood flow baffle design for the outer sphere of the aneurysm. The complex out-of-plane helical coil design is easily packed into an aneurysm and the structure of the coil reduces the incidence of coil compaction, and of coils getting caught on one another preventing the insertion of additional coils. Generally, a vaso occlusive coil is a "coil of a coil." In other words, as used herein, the "primary configuration" refers to the member obtained when a wire is shaped into a coil, for example, as a member to be used to form an occlusive device. The "secondary configuration" refers to the structure obtained when the member in the primary configuration is further shaped, e.g., by winding around a mandrel.

The "free energy state" refers to the theoretical three-dimensional configuration assumed by the member as it would exist with no outside forces on it in its secondary configuration. The "deployed configuration" refers to the shape after the coil has been deployed from the catheter. The deployed configuration of a particular device may differ, depending on whether the device is deployed into the open, or whether it is deployed into a body cavity which may influence the three-dimensional structures. The deployed configurations generally comprise overlapping and intertwining loops or ovals of the strand of the secondary configuration. The loops or ovals can form a closed structure such as an "O" shape (e.g., circle, oval, etc.) or can be open such as a "C" or "U" shape.

Figure 1:
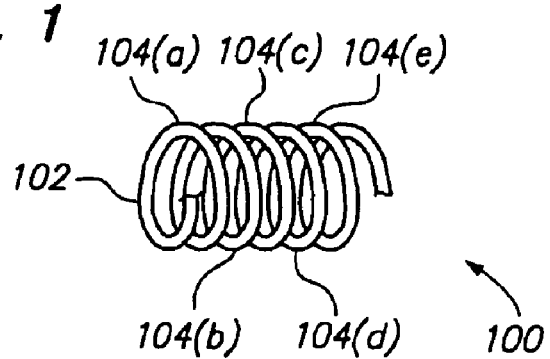
FIG. 1 shows the geometry of an exemplary member for use in forming a vaso-occlusive coil.

FIG. 1 illustrates a member 100 for forming a vaso-occlusive coil. The member 100 comprises a length of wire 102 formed into the primary configuration of a helical microcoil. The wire 102 may be any material suitable for forming a vaso-occlusive device including platinum, rhodium, palladium, tungsten, gold, silver, nitinol, and various alloys of these materials. Preferably, the coil is made from platinum or a platinum-tungsten alloy.

The member 100 is comprised of a series of helices 104(a), 104(b), 104(c), 104(d), 104(e) each having a diameter that is typically 0.125 mm to 0.625 mm. The member 100 is formed by winding the wire 102 under tension onto a cylindrical mandrel. Once formed, the length of the member 100 may range from 5 mm to 1000 mm depending on the application. The amount of tension applied when forming the wire 102, the diameter of the wire 102, the diameter of the helices, and the spacing between the helices, are all variables which determine the stiffness of the member 100. The member 100 may also be constructed such that any of the aforementioned variables will vary along the length of the member.

Figure 2:
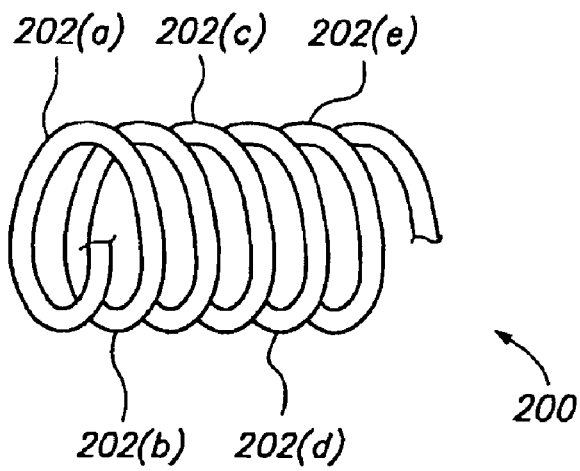
FIG. 2 is a side view of an exemplary helical occlusive coil in a free energy state configuration.

FIG. 2 illustrates a conventional helical vaso-occlusive coil 200 shown in a free energy state. The coil 200 is formed from a member, such as that depicted in FIG. 1. The coil 200 is a helical wound coil having a series of loops 202(a), 202(b), 202(c), 202(d), 202(e). Therefore, in this coil, the secondary configuration is geometrically shaped similar to the member from which it is formed. The loops 202(a), 202(b), 202(c), 202(d), 202(e) may be the same size and shape (as shown) or may vary in size and shape (not shown). Generally the loops 202(a), 202(b), 202(c), 202(d), 202(e) are helices each having a diameter that is typically 2 mm to 20 mm. The number of loops 202(a), 202(b), 202(c) 202(d), 202(e) may vary depending on the desired length of the coil. The length of a conventional helical vaso-occlusive coil typically ranges from 2 cm-80 cm, depending on the application for which it will be used.

Figure 3A:
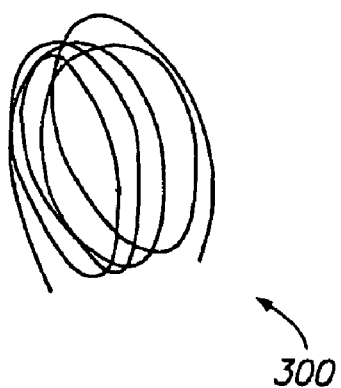
FIG. 3A is a side view of an exemplary helical occlusive coil in a deployed confined state.

A deployed coil formed in a helical secondary shape enters a treatment site, such as an aneurysm, in a helical shaped fashion. FIG. 3A illustrates a deployed vaso-occlusive coil 300, such as that depicted in FIG. 2. The coil 300 is shown in a constrained deployed configuration, meaning it is constrained by a body cavity (not shown) into which it is deployed. The deployed coil 300 remains helical in nature and has an axial length. Such conventional helical coils fail to uniformly fill the peripheral shell "outer sphere" of the aneurysm. Instead coils having this type of structure tend to maintain some degree of axial symmetry when deployed. Subsequently placed coils adopt a similar geometry but not necessarily with the same axial symmetry. This manner of filling leads to non-uniform packing with open void spaces. Poorly packed coil masses are susceptible to rearrangement of the individual coils due to the relatively large amount of free space remaining in the aneurysm. Rearrangements in the architecture of the coil mass may lead to an unfavorable mechanical state which in turn may lead to future recanalization or regrowth of the aneurysm.

Figure 3B:
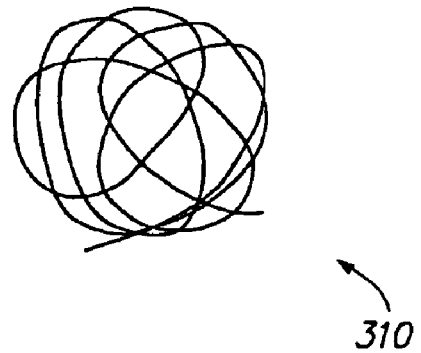
FIG. 3B illustrates an exemplary deployed vaso-occlusive coil in a nearly uniformly distributed shell configuration.

A more desirable situation is to create a coil which expands to fill the inner periphery of an aneurysm in a manner that resembles a uniformly distributed ovoid or spherical shell. FIG. 3B illustrates a deployed vaso-occlusive coil 310 in a nearly uniformly distributed shell configuration. Successively placed coils would then assume the shape of ever-decreasing diameter shells until the aneurysm is substantially filled. Packing of coils in this manner maximizes the filling density and increases the long-term stability of the mass of coils.

Figure 4:
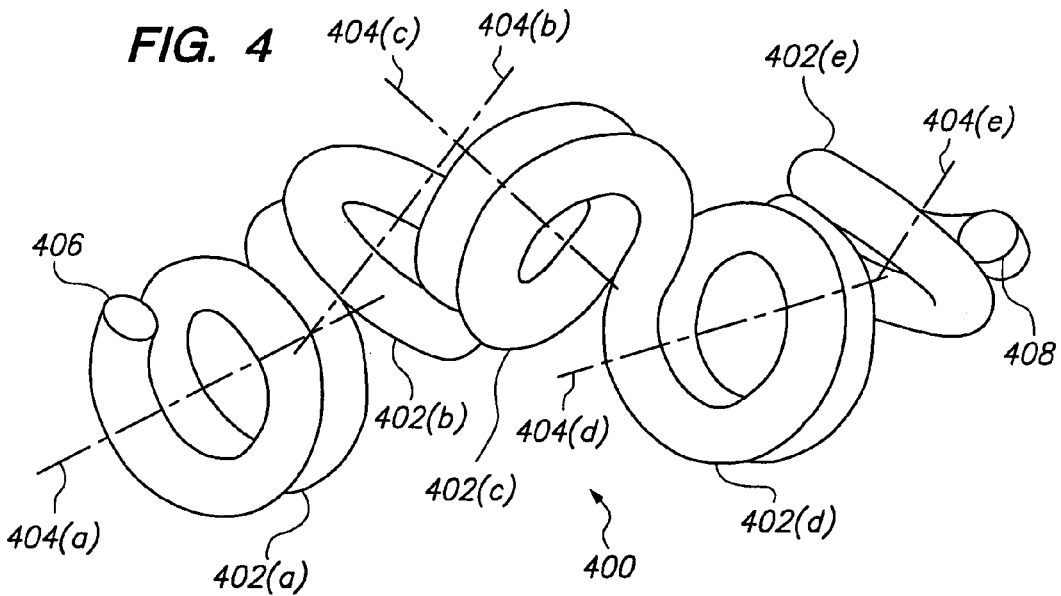
FIG. 4 is a perspective view of a coil in a free energy state in accordance with one embodiment of the invention.

FIG. 4 depicts a vaso-occlusive coil 400 in a free energy state according to an embodiment of the invention. Generally, this coil 400 is described as a complex out-of-plane helical coil. The vaso-occlusive coil 400 is formed from a member, such as that depicted in FIG. 1. The vaso-occlusive coil 400 is a series of loops 402(a), 402(b), 402(c), 402(d). Each loop 402(a-d) lies along a different axis 404(a), 404(b), 404(c), and 404(d), respectively, and in a separate plane from any other loop 402 of the series.

In the illustrated embodiment, coil 400 is formed from a series of loops, where the series has at least four successive loops 402, each having different axis and lying in a separate plane from any other loop 402 in the series, as described above. Adjacent planes, in which the loops lie, form an angle of at least 30 degrees and not more that 90 degrees. Preferably, adjacent planes form an angle of between 45 and 90 degrees and more preferably, each plane is perpendicular to an immediately preceding, or immediately succeeding plane. The coil may be formed from multiple series of loops, depending on the desired overall length of the coil and the application for which it is used.

To create coil 400, a primary member, such as that shown in FIG. 1, is formed into the secondary configuration by heat treatment, which is well known in the art. For example, the member may be initially formed into the secondary configuration by winding or wrapping the member around a suitably sized and shaped mandrel of a refractory material and then subjecting the member to heat treatment for a specific period of time. The resulting secondary configuration is, therefore, made permanent in a free energy state.

Figure 5:
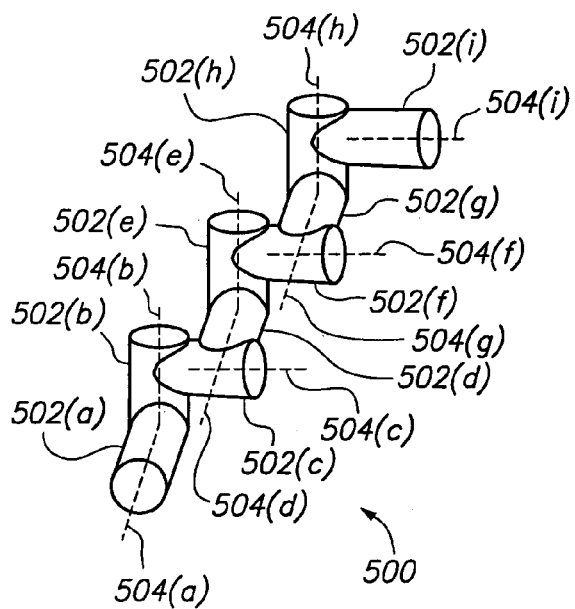
FIG. 5 is a perspective view of a mandrel suitable for winding a coil, according to embodiments of the invention.

FIG. 5 shows a mandrel 500 for use in the manufacture of a vaso-occlusive coil, such as that depicted in FIG. 4. The mandrel is made of a refractory material and includes a series of posts 502(a-i) around which a member having a primary configuration may be wound. At least four of the posts 502(a-d) each have a unique central axis 504(a-d). The posts 502(a-d) are arranged such that the central axis of adjacent posts, e.g., 502(a) and 502(b), are at an angle greater than 30 degrees and not more than 90 degrees, and preferably between 45 degrees and 90 degrees. As shown in FIG. 5, the posts 502(a-d) intersect such that the central axes of any two adjacent posts, e.g., 502(a) and 502(b), are perpendicular to one another. The mandrel 500 is constructed so that a member, such as that depicted in FIG. 1, may be wound in either a clockwise or counterclockwise direction to create the loops. Further, the loops may be created by winding each loop in the same direction, in alternating directions, or in a random selection of directions.

Returning to FIG. 4, each loop 402(a-d) is shown as having a helical form. It will be apparent that, in addition to a helical form, each loop may be formed in an alternate form, such as elliptical or oval. While FIG. 4 shows all loops 402(a-d)

having a similar form, any or each loop 402(a-d) could take on a different form such that the series could be any combination of forms such as helical, oval or elliptical. The size and shape of the loops 402(a-d) is dictated by the size and shape of the periphery of the posts of the mandrel on which a member is wound to create the coil. Therefore, the mandrel posts could be sized and shaped to accommodate any desired combination.

The helical form of the loops 402(a-d) is created by rotating the member about the axis 504(a-d) of the post 502(a-d) on the mandrel 500. Each loop 402(a-d) is constructed by making at least 0.5 rotations and not more than 3.5 rotations about the axis 504(a-d) of the post 502(a-d) on the mandrel 500. In addition, while each loop 402(a-d) as depicted in FIG. 4 is the roughly the same size, in terms of the number of rotations, this is not a limitation of other embodiments of the invention, and the number of rotations constituting a loop may vary by individual loop. In other words, a series of loops could include loops with varying axial length.

While each loop 402(a-e) is depicted as having roughly the same size, it may be desirable to have a distal most loop 402(e) smaller than an immediately successive loop 402(d). A distal loop of a coil is defined as the loop located at a distal end 408, which is the end of the coil 400 which enters the aneurysm first while a proximal end 406 of the coil 400 is that end which is releasably attached to a push wire or other mechanism for moving the coil through a catheter and to a treatment site. When the loops 402(a-e) are helices each has a diameter that is typically 2 mm-20 mm. Loops of varying forms are similarly sized. The length of the coil 400 may vary depending on the application, preferably the length ranges from 2 cm-80 cm.

The vaso-occlusive coil as shown in FIG. 4 is a series of loops directly connected, such that the end of one loop, i.e. 402(a), is immediately connected to the start of the next loop, i.e. 402(b). That is, there is no distinction between where one loop 402(a) ends and the next loop 402(b) begins. A coil formed in this way thereby eliminates any linear sections in the secondary configuration. However, there may be instances in which it is desirable to separate loops, and a member may be wound on a mandrel such that the loops are connected by a curvilinear or linear portion of the member created during the winding process.

Figure 6:
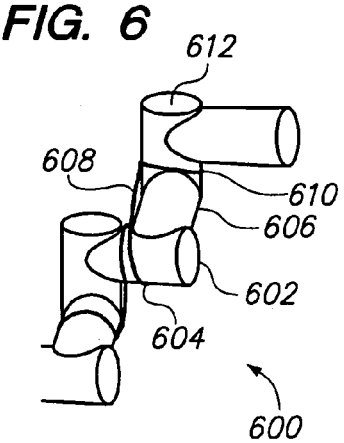
FIG. 6 is a perspective view of a mandrel, wound with a member, for use in forming a coil according to one embodiment of the invention.

As shown in FIG. 6, a mandrel 600, is wound with a member, such as that shown in FIG. 1, to create a linear connection of successive loops. To form such a configuration, the member is wound creating a loop 604 around a post 602. After completing the selected number of rotations of the member about the post 602 (1.25 rotations in the illustrated embodiment), a length 608 of the member is laid axial along the post 606. This length 608 connects the loop 604 created by the winding the member on post 602 to the loop 610 created by successive winding on the adjacent post 612. By constructing the coil in this way, the loops 604 and 610 are connected by a linear segment represented by the length 608 of the portion the member which is laid axially along the post 606.

Figure 7:
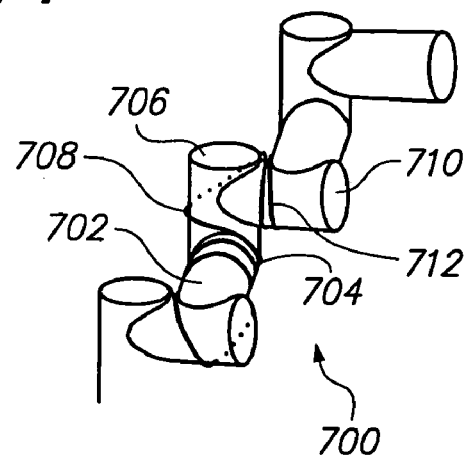
FIG. 7 is a perspective view of a mandrel, wound with a member, for use in forming a coil according to another embodiment of the invention.

Similarly, loops could be connected by a curvilinear segment, as illustrated in FIG. 7. FIG. 7 depicts a mandrel 700 wound with a member, such as that shown in FIG. 1, to create a curvilinear connection of successive loops. In this configuration, a member is wound around a post 702 creating a loop 704. After completing the selected number of rotations of the member about the post 702 (2.25 rotations in the illustrated embodiment), a length of the member 708 is wrapped around the post 706. The length 708 is wrapped such that it extends axially along as well as partially around the periphery of the post 706. This length 708 connects the loop 704 created by the winding the member on post 702 to a loop 712 created by successive winding on the adjacent post 710. By constructing the coil in this way, the loops 704, 712 are connected by a curvilinear segment.

Figure 8:
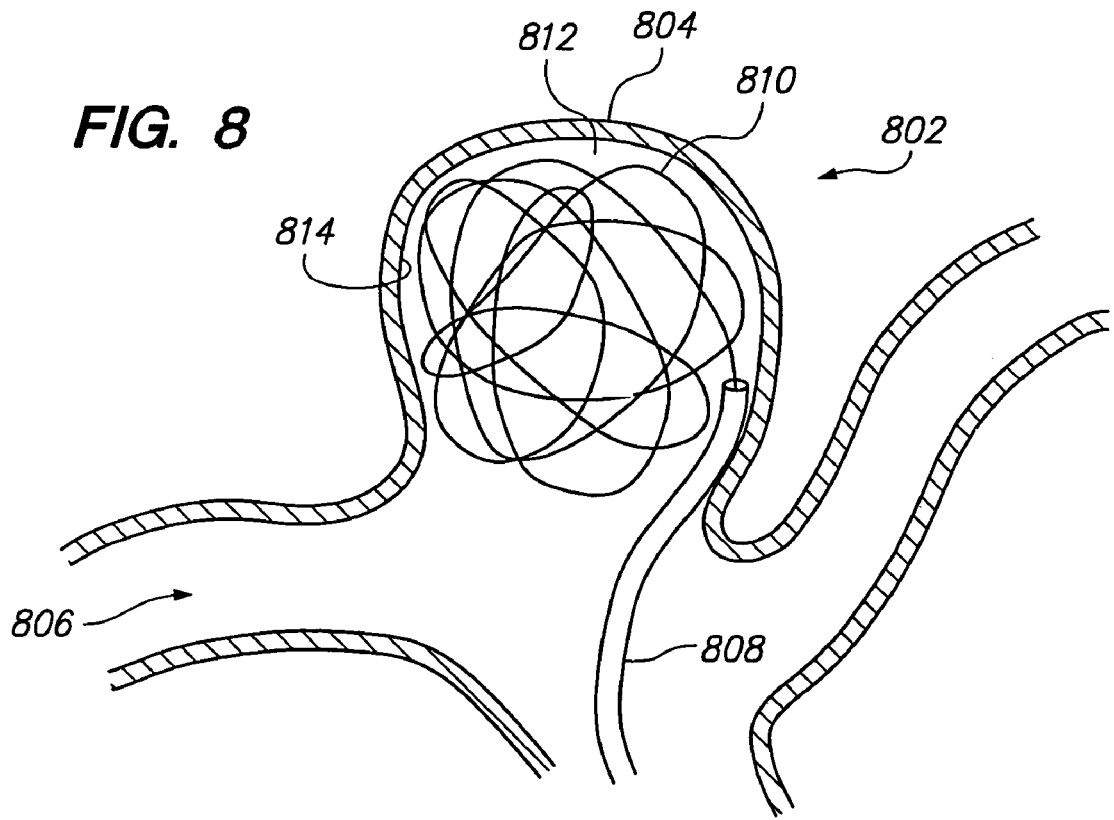
FIG. 8 is a side view of the coil of FIG. 4 in a deployed confined state.

Having described the structure of the coil, the method of using the coil is now described with reference to FIG. 8. In use, a proximal end 406 of the vaso-occlusive coil is attached to a distal end of a guidewire or microcatheter (not shown). The vaso-occlusive coil may be attached and subsequently detached in any known manner, such as by physical pushing, or by electrolytic or mechanical detachment. A target site is visualized by conventional means known in the art. For illustrative purposes, the target site is an aneurysm 802. The aneurysm is defined by a dome 804 coming off a branch of an artery 806. A catheter 808 is inserted in the artery 806, by means known in the art, until it reaches the dome 804. A vaso-occlusive coil 810, such as that shown in FIG. 4, passes through the catheter by means of a guidewire or microcatheter until the vaso-occlusive coil enters the dome 804 of the aneurysm 802.

The end loop (not shown) at the distal end of the vaso-occlusive coil enters the aneurysm 802 first. In some instances, it is desirable to have a smaller loop enter the aneurysm 802 first to ensure the coil remains in the dome, in such a case the end loop is smaller in diameter than the other loops. The remaining loops are then advanced into and fill the aneurysm 802. The diameter of the majority of the loops are approximately the same size as the dome 804, however the entire vaso-occlusive coil is larger than the dome 804 itself and therefore the coil takes on a semi-constrained deployed configuration 810 as it fills the aneurysm 802. The vaso-occlusive coil of the invention is a desirable shape for it tends to fill the interior area 812 of the dome 804 while also filling the peripheral shell of the aneurysm 802.

The deployed coil takes on a more complex, but semi-uniform shape as compared with conventional helical coils. The constrained deployed configuration of the coil is a higher energy state than the unconstrained deployed configuration since the aneurysm 802 constrains the coil. Nonetheless, since the diameter of the loops are approximately the same size as the aneurysm dome, the amount of force required to constrain the coil within the aneurysm dome is kept to a minimum. Once placed, the coil tends to remain in place, constrained by the walls 814 of the dome 804, and further compaction of the coil is minimized. Additional coils may be inserted into the aneurysm until the desired density of coils in the aneurysm is achieved.

As noted previously, the forgoing descriptions of the specific embodiments are presented for purposes of illustration and description, and are not intended to be exhaustive or to limit the invention to the precise forms disclosed, as many modifications and variations are possible in view of the above teachings. The embodiments were chosen and described in order to illustrate and explain principles of the invention and its practical applications, to thereby enable those skilled in the art to best utilize the invention and various embodiments thereof as suited to the particular use contemplated. It is intended that the scope of the invention be defined by the following claims and their equivalents.

What is claimed is:

1. A vaso-occlusive device, comprising:
  a member that forms a series of at least four successive loops, each loop of the series having a different axis than, and lying in a separate plane from, any other loop of the series, and at least two non-successive loops lying in respective planes which are substantially parallel, each of the four successive loops comprising a helical form having 0.5 to 3.5 rotations about its axis; and each plane forming an angle greater than 30 degrees with any immediately proceeding and any immediately succeeding plane.

2. The vaso-occlusive device of claim 1, each plane forming an angle between 45 and 90 degrees with the immediately proceeding and the immediately succeeding plane.

3. The vaso-occlusive device of claim 1, each plane perpendicular to the immediately proceeding and the immediately succeeding plane.

4. The vaso-occlusive device of claim 1, wherein the loops are wound in a clockwise direction.

5. The vaso-occlusive device of claim 1, wherein the loops are wound in a counterclockwise direction.

6. The vaso-occlusive device of claim 1, wherein at least one of the loops is wound in a clockwise direction, and at least one of the loops is wound in a counterclockwise direction.

7. The vaso-occlusive device of claim 1, at least one loop comprising an elliptical form.

8. The vaso-occlusive device of claim 1, at least one loop comprising an oval form.

9. The vaso-occlusive device of claim 1, at least one of the loops having a different geometric form than the other loops.

10. The vaso-occlusive device of claim 1, a distal most loop of the series having a diameter smaller than a diameter of an immediately preceding loop.

* * * * *

UNITED STATES PATENT AND TRADEMARK OFFICE
CERTIFICATE OF CORRECTION

| | | |
|---|---|---|
| PATENT NO. | : 7,485,123 B2 | Page 1 of 1 |
| APPLICATION NO. | : 10/790982 | |
| DATED | : February 3, 2009 | |
| INVENTOR(S) | : Stephen C. Porter | |

It is certified that error appears in the above-identified patent and that said Letters Patent is hereby corrected as shown below:

On column 7, line 2, replace "0.5" with --1.5--

Signed and Sealed this

Twenty-fourth Day of March, 2009

JOHN DOLL
*Acting Director of the United States Patent and Trademark Office*